US012516057B2

(12) United States Patent
Cai et al.

(10) Patent No.: US 12,516,057 B2
(45) Date of Patent: Jan. 6, 2026

(54) CRYSTALLINE FORM OF TLR8 AGONIST

(71) Applicant: CHIA TAI TIANQING PHARMACEUTICAL GROUP CO., LTD., Jiangsu (CN)

(72) Inventors: Zhe Cai, Shanghai (CN); Fei Sun, Shanghai (CN); Charles Z. Ding, Shanghai (CN); Shuhui Chen, Shanghai (CN)

(73) Assignee: CHIA TAI TIANQING PHARMACEUTICAL GROUP CO., LTD, Lianyungang (CN)

( * ) Notice: Subject to any disclaimer, the term of this patent is extended or adjusted under 35 U.S.C. 154(b) by 645 days.

(21) Appl. No.: 17/931,456

(22) PCT Filed: Mar. 18, 2021

(86) PCT No.: PCT/CN2021/081533
§ 371 (c)(1),
(2) Date: Sep. 12, 2022

(87) PCT Pub. No.: WO2021/185312
PCT Pub. Date: Sep. 23, 2021

(65) Prior Publication Data

US 2023/0303557 A1 Sep. 28, 2023

(30) Foreign Application Priority Data

Mar. 18, 2020 (CN) ......................... 202010193418.4

(51) Int. Cl.
*C07D 471/04* (2006.01)

(52) U.S. Cl.
CPC ........ *C07D 471/04* (2013.01); *C07B 2200/13* (2013.01)

(58) Field of Classification Search
CPC ... C07D 471/04; C07B 2200/13; Y02A 50/30; A61P 31/12
See application file for complete search history.

(56) References Cited

U.S. PATENT DOCUMENTS

| | | | | |
|---|---|---|---|---|
| 12,054,482 B2 * | 8/2024 | Cai | A61K 31/549 |
| 2003/0124028 A1 * | 7/2003 | Carlson | C40B 60/14<br>422/68.1 |

FOREIGN PATENT DOCUMENTS

| | | | |
|---|---|---|---|
| WO | WO-2016141092 A1 * | 9/2016 | A61K 31/517 |
| WO | 2020057604 | 3/2020 | |

OTHER PUBLICATIONS

Gardner et al. (Computers and Chemical Engineering 28 (2004) 943-953) (Year: 2004).*
International Search Report and Written Opinion, issued in International Patent Application No. PCT/CN2021/081533, mail date Apr. 26, 2021.

* cited by examiner

*Primary Examiner* — Danah Al-Awadi
*Assistant Examiner* — Chantal Adlam
(74) *Attorney, Agent, or Firm* — Ping Wang; Kalos Athena Wang PLLC

(57) ABSTRACT

Disclosed are a crystalline form of a Toll-like receptor 8 (TLR8) agonist as represented by formula (I) and a preparation method therefor. Further provided is an application of the crystalline form in the preparation of a drug for treating a disease responsive to the TLR8 agonist.

(I)

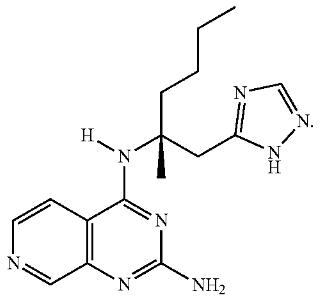

20 Claims, 2 Drawing Sheets

CRYSTALLINE FORM OF TLR8 AGONIST

CROSS-REFERENCE TO RELATED APPLICATIONS

The present application claims priority and benefit to the Chinese Patent Application No. 202010193418.4 filed with National Intellectual Property Administration, PRC on Mar. 18, 2020, the disclosure of which is incorporated herein by reference in its entirety.

BACKGROUND OF THE INVENTION

Technical Field

The present application belongs to the field of medicinal chemistry, and relates to a crystal form of a TLR8 (Toll-like receptor 8) agonist of formula (I) and a method for preparing the same, as well as use of the crystal form for preparing a medicament for treating a disease responsive to TLR8 agonism.

Description of the Related Art

Toll-like receptors (TLRs) are an important class of protein molecules involved in non-specific immunity (innate immunity), and are also a bridge linking non-specific immunity and specific immunity. TLRs are single transmembrane non-catalytic proteins that are expressed primarily in a range of immune cells such as dendritic cells, macrophages, monocytes, T cells, B cells, and NK cells. TLRs are capable of recognizing molecules with conserved structures derived from microorganisms. They can recognize the microorganisms and activate the body to generate immune cell responses when microorganisms break through the physical barriers of the body, such as skin and mucosa. For example, TLR1, TLR2, TLR4, TLR5 and TLR6 mainly recognize extracellular stimuli such as lipopolysaccharide, lipopeptide, and flagellin of bacteria, while TLR3, TLR7, TLR8 and TLR9 function in cell endosomes, such as binding to their ligands after phagocytosis and dissolution of the envelope and recognizing nucleic acids of microorganisms.

Among the different subtypes of TLR, TLR8 has unique functions: TLR8 is expressed primarily in monocytes, macrophages, and myeloid dendritic cells. The signaling pathway of TLR8 can be activated by the single-stranded RNA of bacteria, small-molecule agonists and microRNAs. Activation of TLR8 results in the production of Th1 polar cytokines such as IL-12, IL-18, TNF-α and IFN-γ, and various co-stimulatory factors such as CD80 and CD86. These cytokines can activate and amplify innate and adaptive immune responses and provide a beneficial treatment regimen for diseases involving anti-virus, anti-infection, autoimmunity, tumors, and the like. For example, with respect to hepatitis B, activation of TLR8 on antigen-presenting cells and other immune cells in the liver can activate cytokines such as IL-12, which in turn activates specific T cells and NK cells that are depleted by the virus, thereby reconstituting the antiviral immunity in the liver.

SUMMARY OF THE INVENTION

In one aspect, the present application provides a crystal form of a compound of formula (I),

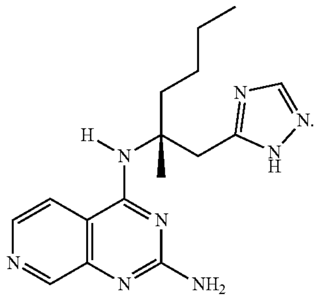

(I)

In some embodiments of the present application, provided is a crystal form A of the compound of formula (I), which has characteristic diffraction peaks at the following 2θ angles in an X-ray powder diffraction pattern: 10.50±0.20°, 20.72±0.20°, and 22.34±0.20°.

In some embodiments of the present application, the crystal form A has characteristic diffraction peaks at the following 2θ angles in an X-ray powder diffraction pattern: 8.86±0.20°, 10.50±0.20°, 11.381.0.20°, 17.80±0.20°, 20.72±0.20°, and 22.34±0.20°.

In some embodiments of the present application, the crystal form A has characteristic diffraction peaks at the following 2θ angles in an X-ray powder diffraction pattern: 8.86±0.20°, 10.50±0.20°, 11.38±0.20°, 13.18±0.20°, 17.80±0.20°, 20.72±0.20°, 22.34±0.20°, and 26.86±0.20°.

In some embodiments of the present application, the crystal form A has characteristic diffraction peaks at the following 2θ angles in an X-ray powder diffraction pattern: 8.86±0.20°, 10.50±0.20°, 11.38±0.20°, 13.18±0.20°, 16.48±0.20°, 17.80±0.20°, 20.36±0.20°, 20.72±0.20°, 22.34±0.20°, 24.42±0.20°, and 26.86±0.20°.

In some embodiments of the present application, the crystal form A has characteristic diffraction peaks at the following 2θ angles in an X-ray powder diffraction pattern: 8.86±0.20°, 10.50±0.20°, 11.38±0.20°, 13.18±0.20°, 16.04±0.20°, 16.48±0.20°, 17.800.20°, 19.96±0.20°, 20.36±0.20°, 20.72±0.20°, 21.92±0.20°, 22.34±0.20°, 23.00±0.20°, 24.42±0.20°, 26.12±0.20°, 26.86±0.20°, and 28.68±0.20°.

In some embodiments of the present application, the crystal form A has XRPD pattern data as shown in Table 1:

TABLE 1

XRPD pattern data for the crystal form A of the compound of formula (I)

| No. | 2θ (±0.20°) | Relative intensity (%) |
|---|---|---|
| 1 | 8.86 | 22.9 |
| 2 | 10.50 | 46.0 |
| 3 | 11.38 | 27.8 |
| 4 | 13.18 | 17.9 |
| 5 | 15.68 | 8.6 |
| 6 | 16.04 | 13.8 |
| 7 | 16.48 | 17.9 |
| 8 | 17.80 | 35.0 |
| 9 | 19.54 | 9.0 |

TABLE 1-continued

| XRPD pattern data for the crystal form A of the compound of formula (I) | | |
|---|---|---|
| No. | 2θ (±0.20°) | Relative intensity (%) |
| 10 | 19.96 | 18.4 |
| 11 | 20.36 | 30.5 |
| 12 | 20.72 | 100.0 |
| 13 | 21.92 | 11.5 |
| 14 | 22.34 | 53.6 |
| 15 | 23.00 | 10.2 |
| 16 | 23.80 | 7.9 |
| 17 | 24.42 | 13.7 |
| 18 | 24.64 | 9.2 |
| 19 | 25.28 | 5.4 |
| 20 | 26.12 | 12.8 |
| 21 | 26.86 | 21.8 |
| 22 | 27.38 | 4.1 |
| 23 | 28.68 | 10.5 |
| 24 | 30.16 | 5.6 |
| 25 | 32.46 | 5.5 |
| / | / | / |

In some embodiments of the present application, the crystal form A has an XRPD pattern as shown in FIG. 1.

In some embodiments of the present application, the crystal form A has a starting point of an endothermic peak at 228.0±5° C. in a differential scanning calorimetry (DSC) curve.

In some embodiments of the present application, the crystal form A has a DSC pattern as shown in FIG. 2.

In some embodiments of the present application, the crystal form A has a weight loss of 0.2261% at 250.00±3° C. in a thermogravimetric analysis (TGA) curve.

In some embodiments of the present application, the crystal form A has a TGA pattern as shown in FIG. 3.

The present application also provides a method for preparing the crystal form A of the compound of formula (I), which comprises:

1) adding the compound of formula (I) into a solvent mixture of acetone and water; and
2) precipitating a solid, and performing filtration to obtain the crystal form A.

In some embodiments of the present application, in the method for preparing the crystal form A, a volume ratio of acetone to water is selected from 1:1 to 1:10; preferably 1:1, 1:2, 1:3, 1:4, 1:5, 1:6, 1:7, 1:8, 1:9 and 1:10 or a range formed by any of the values.

In some embodiments of the present application, the step 1) of the method for preparing the crystal form A further comprises performing stirring at a temperature selected from 25° C. to 60° C., preferably 30° C. to 55° C., and more preferably 40° C. to 50° C.

In some embodiments of the present application, the step 1) of the method for preparing the crystal form A further comprises performing stirring for a period of time selected from 1 hour to 72 hours, preferably 4 hours to 52 hours, and more preferably 8 hours to 32 hours.

In some embodiments of the present application, in the method for preparing the crystal form A, a weight ratio of the compound of formula (I) to the solvents is selected from 1:1 to 1:30.

Some other embodiments of the present application are derived from any combination of the variables as described above.

In another aspect, the present application provides a crystalline composition, comprising the crystal form of the present application, wherein the crystal form accounts for 50% or more, preferably 80% or more, more preferably 90% or more, and most preferably 95% or more, of the weight of the crystalline composition.

In another aspect, the present application provides a pharmaceutical composition, comprising a therapeutically effective amount of the crystal form of the present application, and optionally a pharmaceutically acceptable excipient.

The present application also provides a pharmaceutical composition, comprising a therapeutically effective amount of the crystalline composition of the crystal form of the present application, and optionally a pharmaceutically acceptable excipient.

In another aspect, the present application provides use of the crystal form, the crystalline composition thereof or the pharmaceutical composition thereof for treating a disease responsive to TLR8 agonism.

In another aspect, the present application provides a method for agonizing TLR8, comprising administering to an individual (preferably a human) in need thereof a therapeutically effective amount of the crystal form, the crystalline composition thereof or the pharmaceutical composition thereof of the present application.

In another aspect, the present application provides use of the crystal form, the crystalline composition thereof or the pharmaceutical composition thereof of the present application for preparing a medicament for treating a disease responsive to TLR8 agonism.

In some embodiments of the present application, the disease responsive to TLR8 agonism is selected from viral infection.

In some embodiments of the present application, the viral infection is selected from hepatitis B virus (HBV) infection.

Technical Effects

The compound disclosed herein has significant agonistic activity for TLR8. The compound disclosed herein exhibits desirable agonistic activity and specific selectivity for TLR8. The compound disclosed herein exhibits desirable activity for inducing TLR8 pathway specific cytokines (IL-12p40, IFN-γ). Pharmacokinetic study in mice shows that the compound disclosed herein has moderate oral bioavailability and drug exposure, and thus oral administration is feasible. TLR8 agonist is an immunomodulator, and its excessive exposure may result in immune overactivation of the body, leading to unpredictable side effects.

The crystal form A of the present application is easily available and has good physical stability and chemical stability. In addition, it has good pharmaceutical properties and is suitable for being used as a medicament, and therefore, it has great industrial application value and economic value.

Definitions and Description

Unless otherwise stated, the following terms and phrases used herein are intended to have the following meanings. A particular phrase or term, unless otherwise specifically defined, should not be considered as uncertain or unclear, but construed according to its common meaning. When referring to a trade name, it is intended to refer to its corresponding commercial product or its active ingredient.

The intermediate compounds of the present application can be prepared by a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The chemical reactions of the embodiments disclosed herein are carried out in a proper solvent that must be suitable for the chemical changes in the present application and the reagents and materials required. In order to acquire the compounds disclosed herein, it is sometimes necessary for those skilled in the art to modify or select a synthesis procedure or a reaction scheme based on the existing embodiments.

The present application is described in detail below by way of examples, which are not intended to limit the present application in any way.

All solvents used in the present application are commercially available and can be used without further purification.

The following abbreviations are used in this application:

| | |
|---|---|
| Pd/C | Pd/C catalyst, containing 10 w % palladium |
| DCM | Dichloromethane |
| THF | Tetrahydrofuran |
| Boc | Tert-butyloxycarbonyl, an amine protecting group |
| Cbz | Benzyloxycarbonyl, an amine protecting group |
| DMF | N,N-dimethylformamide |
| TFA | Trifluoroacetic acid |
| PE | Petroleum ether |
| DMSO | Dimethyl sulfoxide |
| EtOH | Ethanol |
| MeOH | Methanol |
| HOAc | Acetic acid |
| Trt | Triphenylmethyl |
| CbzCl | Benzyl chloroformate |
| DIPEA | Diisopropylethylamine |
| $SiO_2$ | 100-200 mesh silica gel powder, for column chromatography |
| psi | Pound force/square inch, unit of pressure |
| p-HPLC | Preparative high performance liquid chromatography, for the purification of compounds |

As used herein, the powder X-ray diffraction (XRPD) in the present application is carried out on a DX-2700BH X-ray diffractometer from Dandong Haoyuan with an X-ray tube: Cu, kα (λ1.54184 Å).

As used herein, the differential scanning calorimetry (DSC) in the present application is carried out on a TA2500 differential scanning calorimeter.

As used herein, the thermogravimetric analysis (TGA) in the present application is carried out on a TA TGA550 thermal gravimetric analyzer.

It should be noted that in the X-ray powder diffraction pattern, the position and relative intensity of a peak may vary due to measuring instruments, measuring methods/conditions, and other factors. For any particular crystal form, the position of a peak may have an error, and the measurement of 2θ may have an error of ±0.2°. Therefore, this error should be considered when determining each crystal form, and crystal forms within this margin of error are within the scope of the present application.

As used herein, the relative intensity of a peak in the XRPD pattern can be calculated from the peak height or the peak area. The relative intensities in the "Table 1. XRPD pattern analytical data for the crystal form A of the compound of formula (I)" are calculated from the peak heights.

It should be noted that, for the same crystal form, the position of an endothermic peak in the DSC pattern may vary due to measuring instruments, measuring methods/conditions, and other factors. For any particular crystal form, the position of an endothermic peak may have an error of ±5° C. or ±3° C. Therefore, this error should be considered when determining each crystal form, and crystal forms within this margin of error are within the scope of the present application.

It should be noted that, for the same crystal form, the position of a weight loss temperature in the TGA pattern may vary due to measuring instruments, measuring methods/conditions, and other factors. For any particular crystal form, the position of a weight loss temperature may have an error of ±5° C. or ±3° C. Therefore, this error should be considered when determining each crystal form, and crystal forms within this margin of error are within the scope of the present application.

The word "comprise" and variations thereof such as "comprises" or "comprising" will be understood in an open, non-exclusive sense, i.e., "including but not limited to".

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio. The term "pharmaceutically acceptable excipient" refers to an inert substance administered with an active ingredient to facilitate administration of the active ingredient, including but not limited to, any glidant, sweetener, diluent, preservative, dye/coloring agent, flavor enhancer, surfactant, wetting agent, dispersant, disintegrant, suspending agent, stabilizer, isotonizing agent, solvent or emulsifier acceptable for use in humans or animals (e.g., domesticated animals) as permitted by the National Medical Products Administration, PRC.

The term "pharmaceutical composition" refers to a mixture consisting of one or more of the compounds disclosed herein or the salts thereof and a pharmaceutically acceptable excipient. The pharmaceutical composition is intended to facilitate the administration of the compound to an organic entity.

Therapeutic dosages of the compound disclosed herein or the crystal form thereof may be determined by, for example, the specific use of a treatment, the route of administration of the compound, the health and condition of a patient, and the judgment ofa prescribing physician. The proportion or concentration of the compound disclosed herein in a pharmaceutical composition may not be constant and depends on a variety of factors including dosages, chemical properties (e.g., hydrophobicity), and routes of administration.

The dosage frequency of the crystal form of the present application depends on needs of an individual patient, e.g., once or twice daily or more times daily. Administration may be intermittent, for example, in a period of several days, the patient receives a daily dose of the crystal form, and in the following period of several days or more days, the patient does not receive the daily dose of the crystal form.

The term "treating" or "treatment" means administering the compound or formulation described herein to ameliorate or eliminate a disease or one or more symptoms associated with the disease, and includes:

(i) inhibiting a disease or disease state, i.e., arresting its development; and (ii) alleviating a disease or disease state, i.e., causing its regression.

For drugs and pharmacological active agents, the term "therapeutically effective amount" refers to an amount of a drug or a medicament that is sufficient to provide the desired effect and is non-toxic. The determination of the effective amount varies from person to person. It depends on the age and general condition of a subject, as well as the particular active substance used. The appropriate effective amount in a case may be determined by those skilled in the art in the light of conventional tests.

Unless otherwise specified clearly herein, singular terms encompass plural terms, and vice versa.

DETAILED DESCRIPTION OF THE INVENTION

Figure 1:
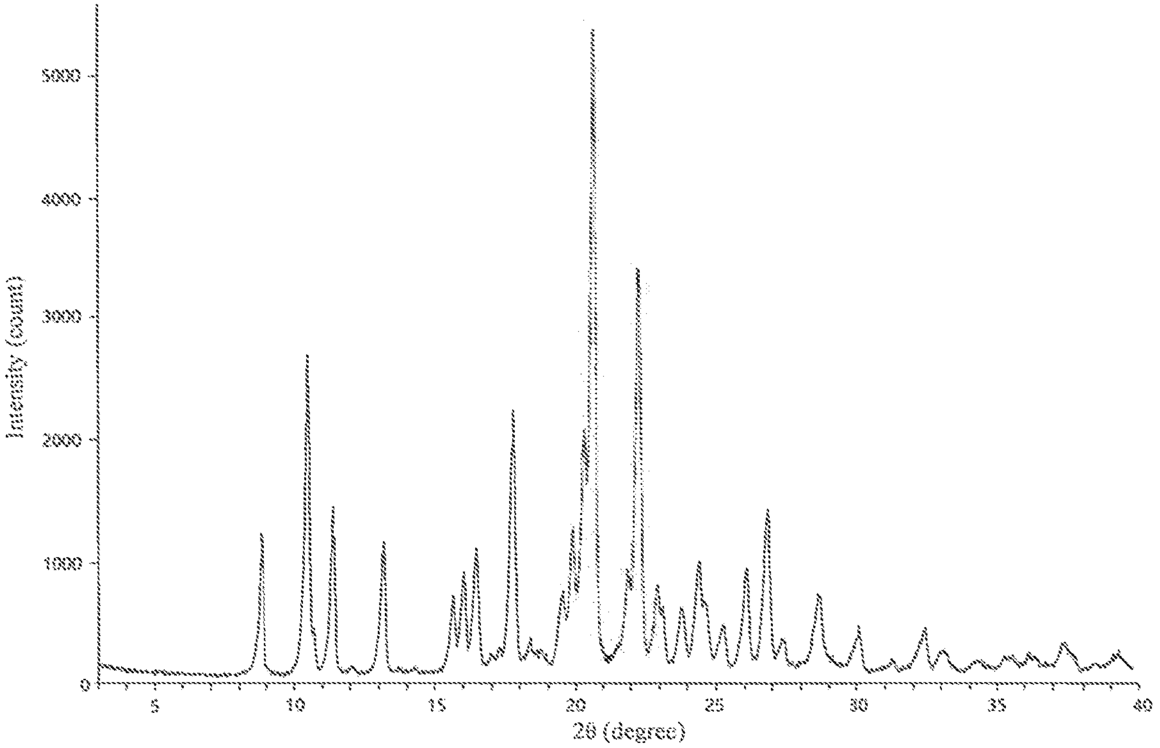
FIG. 1 is an XRPD pattern of the crystal form A of the compound of formula (I).

In order to better understand the content of the present application, further description is given with reference to specific examples, but the specific embodiments are not intended to limit the content of the present application.

Example 1

Preparation of Intermediate 1-10:

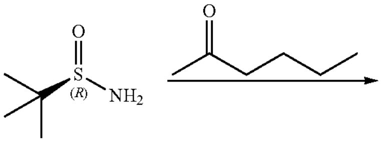

1-1

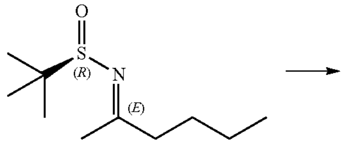

1-2

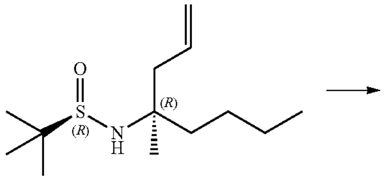

1-3

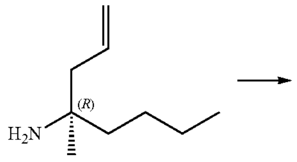

1-4

-continued

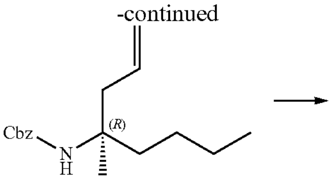

1-5

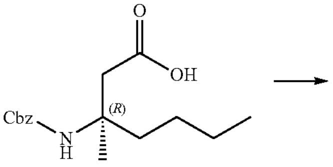

1-6

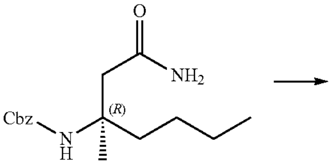

1-7

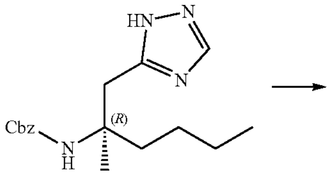

1-8

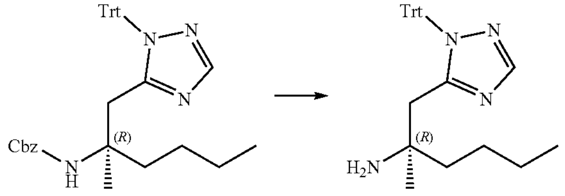

1-9 1-10

Step A: 1-1 (50 g, 412.54 mmol) and tetraethyl titanate (94.10 g, 412.54 mmol, 85.55 mL) were dissolved in THF (500 mL) at 20-30° C., and the solution was added with 2-hexanone (41.32 g, 412.54 mmol, 51.01 mL). The reaction mixture was warmed to 65° C. and stirred for 48 hours, and the resulting reaction mixture was used directly in the next step.

Step B: the reaction mixture in step A was cooled to room temperature, supplemented with THF (1000 mL), then added with allyl bromide (196.33 g, 1.62 mol), and slowly added with zinc powder (53.06 g, 811.43 mmol) in portions. The reaction mixture was stirred at 20-30° C. for 12 hours under nitrogen atmosphere. The reaction mixture was filtered through diatomite, and the filtrate was added with saturated brine (100 mL), stirred, and filtered through diatomite. The resulting filtrate was dried with a rotary evaporator. The residue was dissolved in ethyl acetate (100 mL). The separated organic phase was washed with saturated brine (300 mL×1), dried over anhydrous sodium sulfate, filtered and concentrated under reduced pressure to give a crude product. The crude product was purified by column chromatography ($SiO_2$, PE/EtOAc=15/I to 5/1) to give 1-3. $^1H$ NMR (400 MHz, $CDCl_3$) δ 5.96-5.75 (m, 1H), 5.23-5.08 (m, 2H), 3.20 (s, 1H), 2.39-2.20 (m, 2H), 1.74 (br s, 1H), 1.56-1.42 (m, 2H), 1.40-1.15 (m, 14H), 0.96-0.86 (m, 3H).

Step C: 1-3 (15 g, 61.12 mmol) was dissolved in methanol (150 mL), and the solution was cooled to 0° C. and slowly added with dioxane solution of hydrochloric acid (4 M, 91.68 mL) at 0-20° C. The reaction mixture was stirred at 25° C. for 2 hours. The reaction mixture was directly concentrated under reduced pressure to give 1-4.

Step D: 1-4 (hydrochloride, 13 g, 73.15 mmol) and sodium bicarbonate (55.31 g, 658.36 mmol) were dissolved in dioxane (90 mL) and $H_2O$ (60 mL), and the solution was cooled to 0° C. and then slowly added with CbzCl (74.87 g, 438.91 mmol, 62.40 mL) dropwise. The reaction mixture was warmed to 20-30° C., stirred for 2 hours, and extracted with ethyl acetate (100 mL×2). The organic phases were combined, washed with saturated brine (150 ml×1), dried over anhydrous sodium sulfate, filtered and concentrated under reduced pressure to give a crude product. The crude product was purified by column chromatography ($SiO_2$, PE/EtOAc=I/O to 100/1) to give 1-5. $^1H$ NMR (400 MHz, $CDCl_3$) δ7.30-7.26 (m, 5H), 5.76-5.62 (m, 1H), 5.08-4.91 (m, 4H), 2.47-2.34 (m, 1H), 2.32-2.20 (m, 1H), 1.72-1.57 (m, 1H), 1.50-1.42 (m, 1H), 1.30-1.10 (m, 7H), 0.76-0.76 (m, 1H), 0.76-0.76 (m, 1H), 0.82 (t, J=7.0 Hz, 2H).

Step E: 1-5 (20.8 g, 75.53 mmol) was dissolved in acetonitrile (100 mL), $H_2O$ (150 mL) and carbon tetrachloride (100 mL), and the solution was cooled to 0° C. and slowly added with sodium periodate (64.62 g, 302.12 mmol), followed by the addition of ruthenium trichloride trihydrate (394.99 mg, 1.51 mmol). The reaction mixture was warmed to 25° C. and stirred for 2 hours. The reaction mixture was filtered through diatomite and extracted with DCM (200 mL×1). The organic phase was washed with saturated aqueous sodium sulfite solution (200 mL×1) and saturated brine (200 mL×1) sequentially, dried over anhydrous sodium sulfate, filtered and concentrated under reduced pressure to give crude 1-6, which was used directly in the next step. $^1H$ NMR (400 MHz, $CDCl_3$) δ7.40-7.35 (m, 5H), 5.19 (s, 1H), 5.08 (s, 2H), 2.89 (br d, J 14.5 Hz, 1H), 2.69 (br d, J=14.4 Hz, 1H), 1.90-1.77 (m, 1H), 1.74-1.62 (m, 1H), 1.43-1.20 (m, 7H), 0.90 (t, J=6.9 Hz, 3H).

Step F: 1-6 (20 g, 68.18 mmol) and triethylamine (10.35 g, 102.26 mmol, 14.23 mL) were dissolved in THF (250 mL), and the solution was added with isobutyl chloroformate (9.78 g, 71.59 mmol, 9.40 mL) dropwise at −10° C. under nitrogen atmosphere. The reaction mixture was stirred at −10-0° C. for 30 minutes. The reaction mixture was slowly added with aqueous ammonia (63.70 g, 454.41 mmol, 70 mL, 25%) and stirred at 0-5° C. for 30 minutes. The reaction mixture was concentrated under reduced pressure and extracted with ethyl acetate (200 mL×1). The organic phase was washed with saturated brine (100 mL×2), dried over anhydrous sodium sulfate, filtered and concentrated under reduced pressure to give a crude product. The crude product was purified by column chromatography ($SiO_2$, PE/EtOAc=10/1 to 1/1) to give 1-7. $^1H$ NMR (400 MHz, $CDCl_3$) δ7.41-7.28 (m, 5H), 5.62 (br s, 1H), 5.30-5.12 (m, 2H), 5.11-5.01 (m, 2H), 2.76 (d, J=13.2 Hz, 1H), 2.44 (d, J=13.3 Hz, 11H), 1.85-1.74 (m, 1H), 1.73-1.62 (m, 3H), 1.39-1.29 (m, 5H), 0.90 (t, J=7.0 Hz, 3H). LCMS (ESI) m/z: 293.3 $[M+H]^+$.

Step G: 1-7 (15.34 g, 52.47 mmol) and N,N-dimethylformamide dimethyl acetal (134.55 g, 1.13 mol, 150 mL) were stirred at 120° C. for 2 hours, concentrated under reduced pressure, and dissolved in acetic acid (250 mL), and the solution was slowly added with hydrazine hydrate (25.75 g, 504.09 mmol, 25 mL, 98%). The reaction mixture was stirred at 90° C. for 2 hours under nitrogen atmosphere. The reaction mixture was concentrated under reduced pressure, added with $H_2O$ (400 mL), and extracted with DCM (200 mL×2). The organic phases were combined, washed with saturated brine (200 mL×2), dried over anhydrous sodium sulfate, filtered and concentrated under reduced pressure to give crude 1-8. $^1H$ NMR (400 MHz, $CDCl_3$) δ7.95 (s, 1H), 7.43-7.29 (m, 5H), 5.08 (s, 2H), 4.90 (br s, 1H), 3.42 (br d, J=13.9 Hz, 1H), 3.12 (d, J=14.3 Hz, 1H), 1.87-1.77 (m, 1H), 1.68-1.58 (m, 1H), 1.41-1.17 (m, 7H), 0.90 (br t, J=6.5 Hz, 3H). LCMS (ESI) m/z: 317.2 $[M+H]^+$.

Step H: 1-8 (15.20 g, 48.04 mmol) and DIPEA (12.42 g, 96.08 mmol, 16.74 mL) were dissolved in DCM (160 mL), and the solution was slowly added with triphenylchloromethane (20.09 g, 72.06 mmol). The reaction mixture was stirred at 25° C. for 2 hours. The reaction mixture was added with $H_2O$ (100 mL), added with 2 N diluted hydrochloric acid to adjust the pH (7-8), and extracted with DCM (100 mL×1). The organic phase was washed with saturated brine (100 mL×2), dried over anhydrous sodium sulfate, filtered and concentrated under reduced pressure to give a crude product. The crude product was purified by column chromatography ($SiO_2$, PE/EtOAc=20/1 to 5/1) to give 1-9. $^1H$ NMR (400 MHz, $CDCl_3$) δ7.89 (s, 1H), 7.37-7.27 (m, 14H), 7.18-7.07 (m, 6H), 5.72 (br s, 1H), 5.16-4.93 (m, 2H), 3.07 (d, J=14.2 Hz, 1H), 2.90 (d, J=14.2 Hz, 1H), 1.80-1.61 (m, 4H), 1.33 (s, 3H), 0.90-0.84 (m, 3H). LCMS (ESI) m/z: 559.3 $[M+H]^+$.

Step I: 1-9 (12.75 g, 22.82 mmol) was dissolved in isopropanol (300 mL), and the solution was added with Pd/C (6 g) under nitrogen atmosphere. The suspension was degassed under vacuum and purged with hydrogen three times, and stirred at 25° C. for 16 hours under hydrogen atmosphere (15 psi). The reaction mixture was filtered through diatomite and washed with DCM (300 mL), and the filtrate was concentrated under reduced pressure to give 1-10. $^1H$ NMR (400 MHz, $CDCl_3$) δ7.91 (s, 1H), 7.37-7.28 (m, 9H), 7.17-7.11 (m, 6H), 2.87 (s, 2H), 1.45-1.24 (m, 6H), 1.12 (s, 3H), 0.92-0.84 (m, 3H). LCMS (ESI) m/z: 425.2 $[M+H]^+$.

Synthesis of Hydrochloride of Compound of Formula (I):

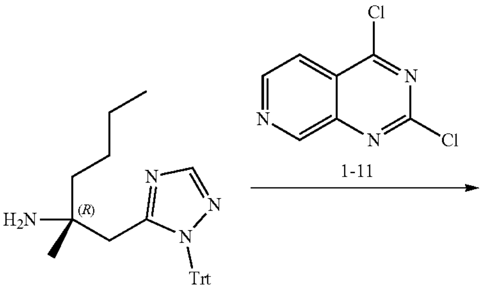
1-11

1-10

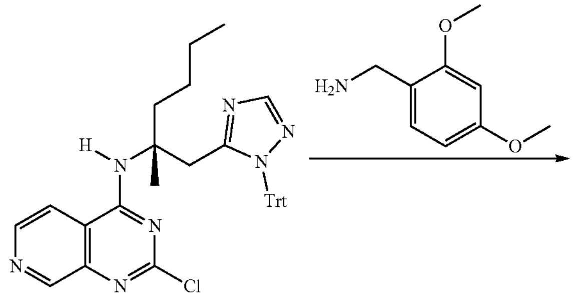

1-12

-continued

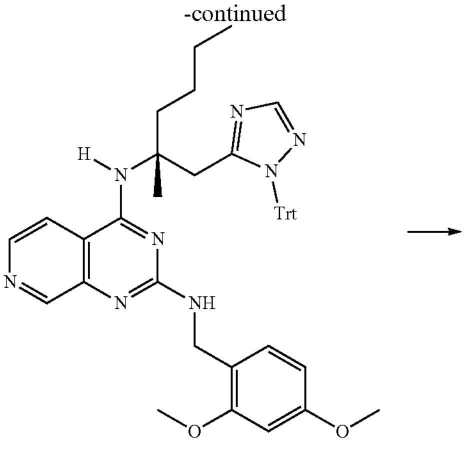

1-13

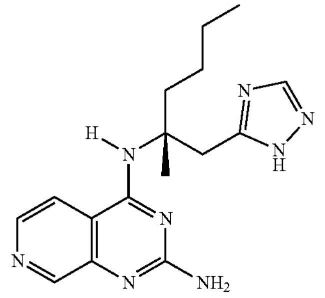

Hydrochloride of compound of formula (I)

Step A: compounds 1-10 (1.91 g, 4.50 mmol) and 1-11 (900 mg, 4.50 mmol) were dissolved in THE (9 mL), and the solution was added with DIPEA (9.00 mmol, 1.57 mL). The reaction mixture was stirred at 70° C. for 3 hours under nitrogen atmosphere. The reaction mixture was concentrated under reduced pressure to give crude 1-12. LCMS (ESI) m/z: 588.42 $[M+H]^+$.

Step B: crude 1-12 (3.60 g, 6.12 mmol) and 2,4-dimethoxybenzylamine (3.01 mg, 18.00 mmol, 2.71 mL) were dissolved in 1,4-dioxane (30 mL), and the solution was added with DIPEA (8.99 mmol, 1.57 mL) under nitrogen atmosphere. The reaction mixture was stirred at 100° C. for 12 hours. The reaction mixture was added with water (20 mL) and ethyl acetate (50 mL) for liquid separation. The organic phase was washed with saturated brine (20 mL), dried over anhydrous sodium sulfate, filtered and concentrated under reduced pressure to give a crude product. The crude product was purified by silica gel column chromatography ($SiO_2$, DCM/MeOH=100/1 to 15/1) to give 1-13. LCMS (ESI) m/z: 719.7 $[M+H]^+$.

Step C: compound 1-13 (2.00 g, 2.78 mmol) and triethylsilane (970.50 mg, 8.35 mmol, 1.33 mL) were dissolved in TFA (41.81 mL), and the solution was stirred at 28° C. for 12 hours. The reaction mixture was directly concentrated under reduced pressure and purified by p-HPLC (column: Phenomenex luna C18 250×50 mm×10 μm; fluidity: [water (0.05% HCl)-acetonitrile]; acetonitrile %: 10%-40%, 28 min, 50% min) to give the hydrochloride of the compound of formula (I). $^1$H NMR (400 MHz, $CD_3OD$) δ9.15 (s, 1H), 8.90 (s, 1H), 8.59 (d, J=5.6 Hz, 1H), 8.26 (d, J=5.5 Hz, 1H), 4.11 (d, J=14.8 Hz, 1H), 3.53 (d, J=14.9 Hz, 1H), 2.60 (dt, J=4.1, 12.8 Hz, 1H), 1.79 (dt, J=4.2, 12.8 Hz, 1H), 1.58 (s, 3H), 1.52-1.19 (m, 4H), 0.92 (t, J=7.2 Hz, 3H). LCMS (ESI) m/z: 327.1 $[M+H]^+$.

Example 2: Preparation of Crystal Form a of Compound of Formula (I)

Figure 2:
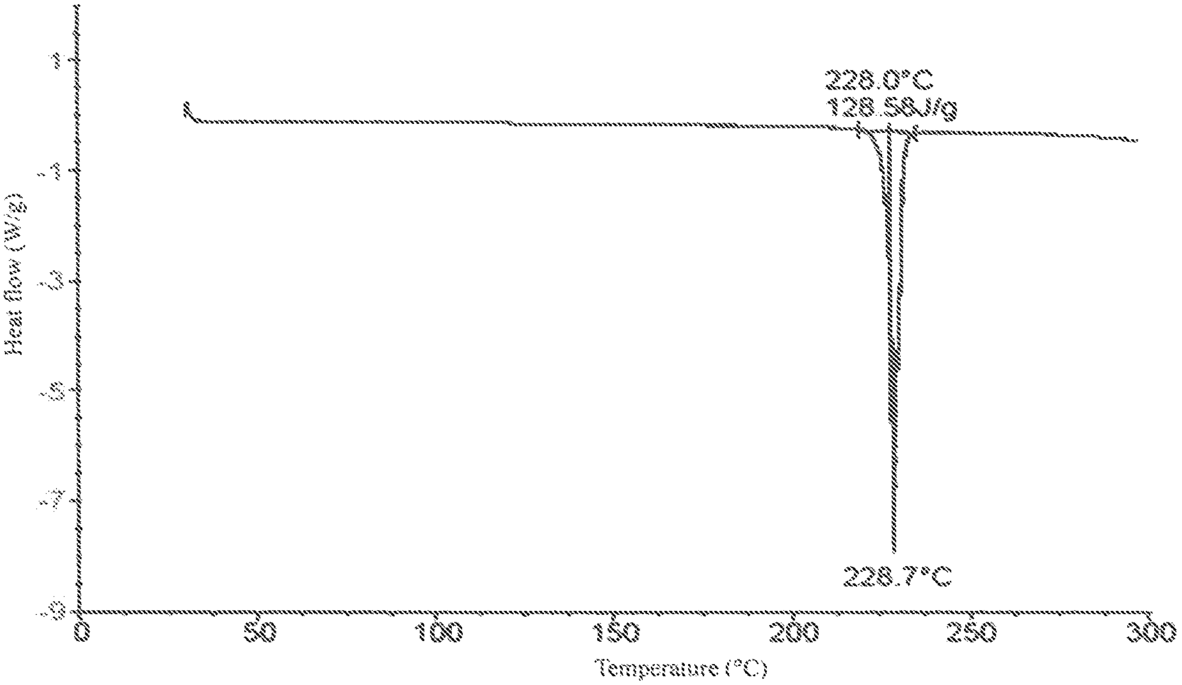
FIG. 2 is a DSC pattern of the crystal form A of the compound of formula (I).
Figure 3:
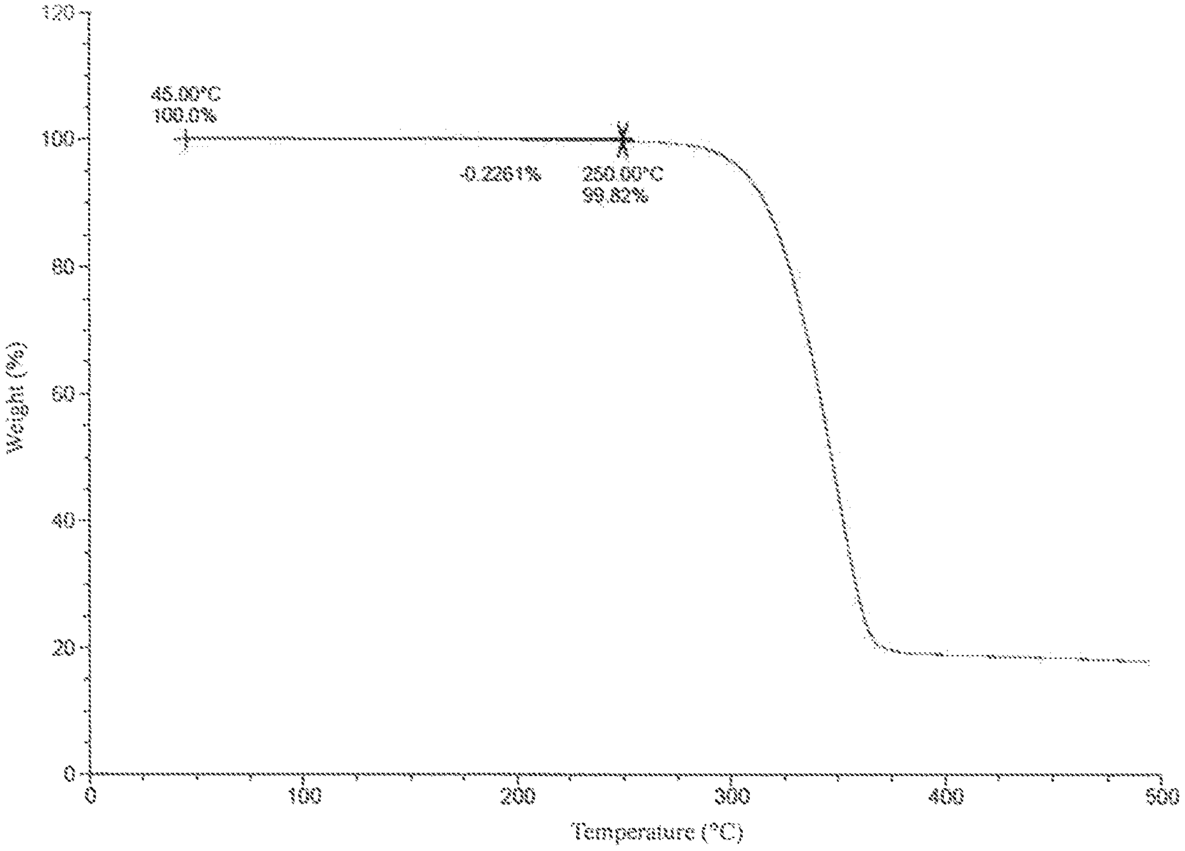
FIG. 3 is a TGA pattern of the crystal form A of the compound of formula (I).

The hydrochloride of the compound of formula (I) (1.4 g) was added to water (50 mL), and the pH was adjusted to 9-10 with solid sodium carbonate. The mixture was extracted with ethyl acetate (50 mL×2). The extract was concentrated, and acetone (10 mL) and water (10 mL) were added to the concentrate. The mixture was stirred at 25° C. for 1 hour, concentrated under reduced pressure to remove acetone (about 8 mL), and stirred at room temperature (15-25° C.) for about 1 hour, and a solid precipitated. The mixture was filtered, and the filter cake was dried in a vacuum drying oven (45° C., 16 hours) to give the crystal form A as a white solid. FIG. 1 shows an XRPD pattern of the crystal form, FIG. 2 shows a DSC pattern of the crystal form, and FIG. 3 shows a TGA pattern of the crystal form.

Experimental Example 1: Screening for In Vitro Receptor Binding Activity of Human Toll-Like Receptor 7 (TLR7) and Human Toll-Like Receptor 8 (TLR8)

The HEK-Blue™ hTLR7 (catalog No.: hkb-htlr7) and HEK-Blue™ hTLR8 (catalog No.: hkb-htlr8) cell lines used in this experiment were purchased from InvivoGen. The two cell lines were constructed by a human embryonic kidney 293 cell line stably co-transfecting hTLR7 or hTLR8 and inducing expression of Secreted Alkaline Phosphatase (SEAP) reporter gene, wherein SEAP reporter gene was regulated by an IFN-β promoter. The promoter was fused with NF-κB and AP-1 binding sites. hTLR7 or hTLR8 agonist could activate NF-κB and AP-1 and induce the expression and secretion of SEAP. The agonistic activity of compound for hTLR7 and hTLR8 receptors was identified by measuring the expression level of SEAP using QUANTI-Blue™ reagent.

Procedures:

1. The compound was added to a cell plate in a 3-fold gradient, with 10 concentrations (5000 nM, 1667 nM, 556 nM, 185 nM, 62 nM, 21 nM, 6.9 nM, 2.3 nM, 0.76 nM, and 0.25 nM) obtained, and two duplicate wells were set for each concentration. 1 μL of DMSO was added to each negative control well.
2. The cells cultured in a T150 flask were taken out from a $CO_2$ incubator, and the cell culture supernatant was discarded. The resulting cells were washed once with Dulbecco's phosphate buffered saline (DPBS). The flask was added with about 10 mL of the culture medium, and tapped to detach the cells. The resulting cell mass was gently pipetted evenly. The cells were counted and the cell suspension was adjusted to 500,000 cells/mL with the culture medium. Then 100 μL of diluted cells (50,000 cells/well) were added to each well of a 96-well plate containing the compound.
3. The compound and cells were co-incubated in an incubator at 37° C. with 5% $CO_2$ for 24 hours.
4. Activity assay on the compound: 20 μL of the induced cell supernatant from each well was added to a cell culture plate containing 180 μL of QUANTI-Blue™ reagent, and after incubation at 37° C. for 1 hour, the optical density absorbance at 650 nm ($OD_{650}$) was assayed for each well using a multi-functional microplate reader.

5. Activity assay on the cells: luciferase signal (RLU) was detected using a multi-functional microplate reader as per the process described in the instructions of ATPlite 1Step.
6. Data analysis: compound activity: $OD_{650}$ values were analyzed using a GraphPad Prism software and the dose-response curves of the compound were fitted to calculate $EC_{50}$ values (half maximal effect concentration) for the compound.

Experimental results: the results are shown in Table 2.

TABLE 2

| Test compound | Human TLR8 $EC_{50}$ (μM) | Human TLR7 $EC_{50}$ (μM) |
|---|---|---|
| Hydrochloride of compound of formula (I) | 0.003 | 33.33 |

Conclusion: the compound disclosed herein exhibits desirable TLR8 agonist activity and, in terms of TLR8 and TLR7, has specific selectivity for TLR8.

Experimental Example 2: Experimental Procedure for Peripheral Blood Mononuclear Cell TLR8 is a receptor for the innate immune system to sense exogenous pathogens, and can recognize exogenous viral single-stranded RNA and cause the release of a series of cytokines such as TNF-α, IL-12, and IFN-γ to elicit an antiviral immune response; TLR7 is another receptor for the innate immune system to sense exogenous pathogens and, when activated, produces primarily such antiviral cytokines as IFN-α. In this experiment, a potential compound of TLR8 agonist was used to stimulate human peripheral blood mononuclear cells (hPBMCs), and the levels of TNF-α, IL-12p40, IFN-γ and IFN-α above were measured to reflect the activation of the compound on TLR8 receptor and its selectivity for TLR8/TLR7.

Procedures:

1. Fresh blood of healthy volunteers was collected, and anticoagulated with an EDTA-K2 anticoagulation tube (catalog No.: BD-8516542);
2. hPBMCs in the middle cloud-like layer were separated after Ficoll density gradient centrifugation, and washed twice with RPMI1640 (source: Gibco, catalog No.: 224400-089) containing 10% serum, and the culture medium was resuspended to 10 mL. After the cells were counted with Vi-cell cell counter, the concentration of cell suspension was adjusted to $2\times10^6$/mL;
3. The compound was dissolved in DMSO to 100 mM, and diluted to 50 mM and 2 mM with DMSO, which were served as initial concentrations. Then the solutions were each diluted sequentially in a 3-fold gradient (sample at a previous concentration (5 μL)+DMSO (10 μL)) to obtain 8 gradients. The resulting solutions were each subjected to 500-fold dilution with the culture medium to prepare the working solutions of the compound;
4. 100 μL of hPBMC suspension and 100 μL of compound working solution were added to each well of a U-bottom 96-well plate, with the final concentrations being 2000 nM, 666.7 nM, 222.2 nM, 74.1 nM, 24.7 nM, 8.2 nM, 2.7 nM and 0.9 nM, respectively, and incubated for 24 hours. Then the supernatants were collected and cryopreserved at −20° C. for the detection of TNF-α, IFN-γ and IL-12p40 cytokines. The other group of compound samples, with the final concentrations being 50 μM, 16.7 μM, 5.6 μM, 1.9 μM, 0.6 μM, 0.2 μM, 0.1 μM and 0.02 μM, respectively, were incubated for 24 hours. The supernatants were collected and cryopreserved at −20° C. for the detection of IFN-α cytokines;
5. IL-12p40, TNF-α and IFN-γ in the supernatant were detected by flow cytometric bead array (CBA); IFN-α in the cell supernatant was detected by enzyme-linked immuno sorbent assay (ELISA).
6. Data analysis: compound activity: $EC_{50}$ values (half maximal effect concentration) were analyzed using a GraphPad Prism software and the dose-response curves of the compound were fitted to calculate $EC_{50}$ values for the compound.

Experimental results: the results are shown in Table 3.

TABLE 3

| Test compound | IL-12p40 $EC_{50}$ (nM) | IFN-γ $EC_{50}$ (nM) | TNF-α $EC_{50}$ (nM) | IFN-α $EC_{50}$ (nM) |
|---|---|---|---|---|
| Hydrochloride of compound of formula (I) | 26 | 29 | 105 | 2800 |

Conclusion: the compound disclosed herein has desirable induction activity for TLR8 pathway specific cytokines IL-12p40, TNF-α and IFN-γ, and relatively low induction activity for TLR7 pathway specific cytokine IFN-α, showing desirably specific selectivity for TLR8 pathway activation.

Experimental Example 3: Pharmacokinetic Study in Mice

This experiment was intended to evaluate the pharmacokinetic behavior of the compound after a single intravenous injection or intragastric administration in mice. Intravenous injection: the test compound was prepared into a 0.5 mg/mL clear solution, with the vehicle being 5% DMSO/5% polyethylene glycol-15 hydroxystearate/90% water; intragastric administration: the test compound was prepared into a 2 mg/mL suspension, with the vehicle being 0.5% sodium carboxymethylcellulose/0.2% tween 80/99.3% water.

The concentration of the test compound in plasma was determined by high performance liquid chromatography-tandem mass spectrometry (LC-MS/MS). The retention times of the compound and internal standard, chromatogram acquisitions and integrals of chromatograms were processed using the software Analyst (Applied Biosystems), and the data statistics were processed using the software Watson LIMS (Thermo Fisher Scientific) or Analyst (Applied Biosystems).

The plasma concentrations were processed using a non-compartmental model of WinNonlin™ Version 6.3 (Pharsight, Mountain View, CA), a pharmacokinetic software, and the pharmacokinetic parameters were calculated using a linear-log trapezoidal method.

The related pharmacokinetic parameters in the mice at 1 mg/Kg intravenous injection and 5 mg/Kg oral intragastric administration of the hydrochloride of the compound of formula (I) are shown in Table 4 below.

TABLE 4

| | | |
|---|---|---|
| Intravenous injection (1 mg/Kg) | Cl (mL/min/kg) | 90.2 |
| | Vdss (L/kg) | 1.75 |
| | $t_{1/2}$ (hour) | 0.25 |
| | $AUC_{0\text{-}last}$ (nM · hr) | 450 |
| Oral intragastric administration (5 mg/Kg) | $T_{max}$ (hour) | 0.5 |
| | $C_{max}$ (nM) | 421 |
| | $AUC_{0\text{-}last}$ (nM · hr) | 624 |
| Bioavailability (F %) | | 27.7 |

Experimental Example 4: Stability Testing

1. Influencing Factor Testing

Test Sample:

the crystal form A of the compound of formula (I)

1) Photostability Testing

Two test samples (one as a 5-day test sample, the other as a 10-day test sample) and two controls (one as a 5-day control, the other as a 10-day control) were used. The test samples were spread as thin layers on clean watch glasses and covered with quartz glass covers. The controls were packaged in the same manner as the test samples except that the watch glasses were covered with aluminum film.

Test conditions: a photostability tester.

The photostability test results are detailed in Table 5.

TABLE 5

Photostability test results

| Test items | Initial value | Photostability tests Day 5 Control group | | Day 10 Control group | |
|---|---|---|---|---|---|
| | | Control group | Test group | Control group | Test group |
| Appearance | Off-white powder | Off-white powder | Off-white powder | Off-white powder | Off-white powder |
| Content | 98.3% | 98.7% | 98.8% | 99.1% | 98.6% |
| Total impurity content | <0.05% | <0.05% | <0.05% | <0.05% | <0.05% |
| Enantiomer | 0.34% | 0.35% | 0.34% | 0.36% | 0.34% |
| Water | 0.19% | 0.25% | 0.24% | 0.25% | 0.25% |

The above results show that there was no significant change in the 5-day and 10-day test items with respect to the initial values under lighting conditions, indicating that the crystal form A has good photostability.

2) Testing for the Effect of Temperature

Each sample was placed on an open watch glass and tested under high-temperature conditions (60° C.)

The high-temperature test results are detailed in Table 6.

TABLE 6

High-temperature (60° C.) test results

| Test items | 60° C. Initial value | Day 5 | Day 10 | Day 30 |
|---|---|---|---|---|
| Appearance | Off-white powder | Off-white powder | Off-white powder | Off-white powder |
| Content | 98.3% | 99.1% | 99.0% | 98.2% |
| Total impurity content | <0.05% | <0.05% | <0.05% | <0.05% |
| Enantiomer | 0.34% | 0.35% | 0.37% | 0.34% |
| Water | 0.19% | 0.25% | 0.24% | 0.26% |

The above results show that there was no significant change in the 5-day, 10-day and 30-day test items with respect to the initial values under high-temperature conditions, indicating that the crystal form A has good high-temperature stability.

3) Testing for the Effect of Humidity

Each sample was placed in an open low-form weighing bottle and tested under high-humidity conditions (25° C./92.5 RH).

The high-humidity test results are detailed in Table 7.

TABLE 7

The results of the testing for the effect of high humidity (25° C./92.5 RH)

| Test items | 25° C./92.5 RH Initial value | Day 5 | Day 10 | Day 30 |
|---|---|---|---|---|
| Appearance | Off-white powder | Off-white powder | Off-white powder | Off-white powder |
| Content | 98.3% | 98.8% | 99.4% | 98.7% |
| Total impurity content | <0.05% | <0.05% | <0.05% | <0.05% |
| Enantiomer | 0.34% | 0.35% | 0.35% | 0.35% |
| Water | 0.19% | 0.29% | 0.29% | 0.30% |

The above results show that there was no significant change in the 5-day, 10-day and 30-day test items with respect to the initial values under high-humidity conditions, indicating that the crystal form A has good high-humidity stability.

2. Accelerated Testing

Test Sample:

the crystal form A of the compound of formula (I)

The Packaging Form:

Inner packaging: a double-layer medical low-density polyethylene bag; outer packaging: an aluminum foil bag.

Test conditions: 40±2° C./75±5% RIH.

The accelerated test results are detailed in Table 8.

TABLE 8

Accelerated test (40 ± 2° C./75 ± 5% RH) results

| Test items | Test time Initial value | Month 1 | Month 2 | Month 3 | Month 6 |
|---|---|---|---|---|---|
| Appearance | Off-white powder | Off-white powder | Off-white powder | Off-white powder | Off-white powder |
| Content | 98.3% | 98.9% | 99.5% | 98.8% | 99.3% |
| Total impurity content | <0.05% | <0.05% | <0.05% | <0.05% | <0.05% |

TABLE 8-continued

| Accelerated test (40 ± 2° C./75 ± 5% RH) results | | | | | |
|---|---|---|---|---|---|
| | Test time | | | | |
| Test items | Initial value | Month 1 | Month 2 | Month 3 | Month 6 |
| Enantiomer | 0.34% | N/A | N/A | 0.32% | 0.34% |
| Water | 0.19% | 0.30% | 0.31% | 0.28% | 0.34% |
| XRPD | Crystal form A | N/A | N/A | Crystal form A | N/A |

Note:
N/A indicates no detection.

The XRPD results show that there was no significant change at month 3 with respect to the initial values, indicating that the crystal form A stays stable under accelerated conditions.

What is claimed is:

1. A crystal form of a compound of formula (I),

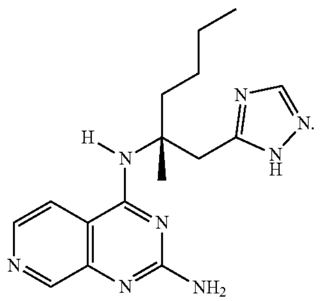

(I)

2. The crystal form according to claim 1, wherein the crystal form has characteristic diffraction peaks at the following 2θ angles in an X-ray powder diffraction pattern: 10.50±0.20°, 20.72±0.20°, and 22.34±0.20°;

or wherein the crystal form has characteristic diffraction peaks at the following 2θ angles in the X-ray powder diffraction pattern: 8.86±0.20°, 10.50±0.20°, 11.38±0.20°, 17.80±0.20°, 20.72±0.20°, and 22.34±0.20°;

or wherein the crystal form has characteristic diffraction peaks at the following 2θ angles in the X-ray powder diffraction pattern: 8.86±0.20°, 10.50±0.20°, 11.38±0.20°, 13.18±0.20°, 17.80±0.20°, 20.72±0.20°, 22.34±0.20°, and 26.86±0.20°;

or wherein the crystal form has characteristic diffraction peaks at the following 2θ angles in the X-ray powder diffraction pattern: 8.86±0.20°, 10.50±0.20°, 11.38±0.20°, 13.18±0.20°, 16.48±0.20°, 17.80±0.20°, 20.36±0.20°, 20.72±0.20°, 22.34±0.20°, 24.42±0.20°, and 26.86±0.20°;

or wherein the crystal form has characteristic diffraction peaks at the following 2θ angles in the X-ray powder diffraction pattern: 8.86±0.20°, 10.50±0.20°, 11.38±0.20°, 13.18±0.20°, 16.04±0.20°, 16.48±0.20°, 17.80±0.20°, 19.96±0.20°, 20.36±0.20°, 20.72±0.20°, 21.92±0.20°, 22.34±0.20°, 23.00±0.20°, 24.42±0.20°, 26.12±0.20°, 26.86±0.20°, and 28.68±0.20°.

3. The crystal form according to claim 2, wherein the crystal form has an XRPD pattern as shown in FIG. 1.

4. The crystal form according to claim 1, wherein the crystal form has a starting point of an endothermic peak at 228.0±5° C. in a differential scanning calorimetry curve.

5. The crystal form according to claim 4, wherein the crystal form has a DSC pattern as shown in FIG. 2.

6. The crystal form according to claim 1, wherein the crystal form has a weight loss of 0.2261% at 250.00±3° C. in a thermogravimetric analysis curve.

7. The crystal form according to claim 6, wherein the crystal form has a TGA pattern as shown in FIG. 3.

8. A method for preparing the crystal form according to claim 2, comprising:

1) adding the compound of formula (I) to a solvent mixture of acetone and water; and
2) precipitating a solid; and
3) performing filtration to obtain the crystal form.

9. The method according to claim 8, wherein the solvent mixture has an acetone:water volume ratio in the range of 1:1 to 1:10.

10. The method according to claim 8, wherein step 1) further comprises performing stirring at a temperature in the range of 25° C. to 60° C.

11. The method according claim 8, wherein step 1) further comprises performing stirring for a period of time in the range of 1 hour to 72 hours.

12. The method according to claim 8, wherein the compound of formula (I) is added to the solvent mixture at a compound of formula (I): solvent mixture weight ratio in the range of 1:1 to 1:30.

13. A crystalline composition, comprising the crystal form according to claim 1, wherein the crystal form accounts for:

50% or more by weight of the crystalline composition, or
80% or more by weight of the crystalline composition, or
90% or more by weight of the crystalline composition, or
95% or more by weight of the crystalline composition.

14. A pharmaceutical composition, comprising a therapeutically effective amount of the crystal form according to claim 1, and optionally a pharmaceutically acceptable excipient.

15. A method for treating a disease responsive to TLR8 agonism, comprising administering to an individual in need thereof a therapeutically effective amount of the crystal form according to claim 1.

16. The method according to claim 15, wherein the disease responsive to TLR8 agonism is a viral infection.

17. The method according to claim 16, wherein the viral infection is hepatitis B virus infection.

18. The method according to claim 9, wherein the acetone:water volume ratio is selected from the group consisting of 1:1, 1:2, 1:3, 1:4, 1:5, 1:6, 1:7, 1:8, 1:9 and 1:10.

19. The method according to claim 10, wherein the temperature is in the range of 30° C. to 55° C., or in the range of 40° C. to 50° C.

20. The method according to claim 11, wherein the period of time is in the range of 4 hours to 52 hours, or in the range of 8 hours to 32 hours.

* * * * *